United States Patent
Furukawa et al.

(10) Patent No.: US 9,436,994 B2
(45) Date of Patent: Sep. 6, 2016

(54) IMAGE PROCESSING APPARATUS FOR PROCESSING A TOMOGRAM OF AN EYE TO BE EXAMINED, IMAGE PROCESSING METHOD, AND COMPUTER-READABLE STORAGE MEDIUM

(75) Inventors: Daisuke Furukawa, Koganei (JP); Hiroshi Imamura, Tokyo (JP); Yoshihiko Iwase, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 631 days.

(21) Appl. No.: 13/375,171

(22) PCT Filed: May 13, 2010

(86) PCT No.: PCT/JP2010/058491
§ 371 (c)(1),
(2), (4) Date: Nov. 29, 2011

(87) PCT Pub. No.: WO2010/140477
PCT Pub. Date: Dec. 9, 2010

(65) Prior Publication Data
US 2012/0070059 A1    Mar. 22, 2012

(30) Foreign Application Priority Data
Jun. 2, 2009 (JP) ................................. 2009-133453

(51) Int. Cl.
*G06K 9/00* (2006.01)
*G06T 7/00* (2006.01)
*A61B 3/10* (2006.01)

(52) U.S. Cl.
CPC ............. *G06T 7/0014* (2013.01); *A61B 3/102* (2013.01); *G06T 2207/10101* (2013.01); *G06T 2207/20036* (2013.01); *G06T 2207/30041* (2013.01)

(58) Field of Classification Search
CPC .. A61B 3/0025; A61B 3/1005; A61B 3/102; A61B 3/14; G06T 2207/10101; G06T 2207/30041
See application file for complete search history.

(56) References Cited

U.S. PATENT DOCUMENTS 7,347,548 B2 *   3/2008  Huang ................... A61B 3/102
                                                         351/205

(Continued)

FOREIGN PATENT DOCUMENTS

| CN | 101084824 A | 12/2007 |
|----|-------------|---------|
| EP | 1864608 A1  | 12/2007 |

(Continued)

OTHER PUBLICATIONS

H. Sanchez-Tocino et al, "Retinal Thickness Study with Optical Coherence Tomography in Patients with Diabetes", Investigative Ophthalmology & Visual Science, May 2002, vol. 43, No. 5, p. 1588-1594.*

(Continued)

*Primary Examiner* — Gandhi Thirugnanam
(74) *Attorney, Agent, or Firm* — Carter, DeLuca, Farrell & Schmidt, LLP

(57) ABSTRACT

An image processing apparatus comprising, boundary extraction means for detecting boundaries of retina layers from a tomogram of an eye to be examined, exudate extraction means for extracting an exudate region from a fundus image of the eye to be examined, registration means for performing registration between the tomogram and the fundus image, and calculating a spatial correspondence between the tomogram and the fundus image, specifying means for specifying a region where an exudate exists in the tomogram using the boundaries of the retina layers, the exudate region, and the spatial correspondence, likelihood calculation means for calculating likelihoods of existence of the exudate in association with the specified region, and tomogram exudate extraction means for extracting an exudate region in the tomogram from the specified region using the likelihoods.

20 Claims, 10 Drawing Sheets

(56) References Cited

U.S. PATENT DOCUMENTS

| | | | |
|---|---|---|---|
| 8,687,863 B2* | 4/2014 | Takama | A61B 3/102 128/922 |
| 8,693,749 B2* | 4/2014 | Nakano | G06T 7/0012 351/206 |
| 8,764,189 B2* | 7/2014 | Stetson | 351/205 |
| 2005/0018133 A1* | 1/2005 | Huang et al. | 351/205 |
| 2005/0123197 A1* | 6/2005 | Tank | G06K 9/00201 382/173 |
| 2006/0119858 A1* | 6/2006 | Knighton | A61B 3/102 356/479 |
| 2006/0253002 A1* | 11/2006 | Kolanko et al. | 600/300 |
| 2006/0257031 A1* | 11/2006 | Abramoff | G06K 9/6277 382/224 |
| 2007/0002275 A1* | 1/2007 | Yan et al. | 351/200 |
| 2007/0115481 A1* | 5/2007 | Toth et al. | 356/511 |
| 2007/0195269 A1* | 8/2007 | Wei et al. | 351/221 |
| 2007/0216909 A1* | 9/2007 | Everett | A61B 5/0059 356/479 |
| 2007/0222946 A1* | 9/2007 | Fukuma et al. | 351/206 |
| 2007/0285619 A1* | 12/2007 | Aoki et al. | 351/206 |
| 2008/0030680 A1* | 2/2008 | Tsukada et al. | 351/206 |
| 2008/0100612 A1* | 5/2008 | Dastmalchi et al. | 345/418 |
| 2008/0204655 A1* | 8/2008 | Kikawa et al. | 351/206 |
| 2009/0161826 A1* | 6/2009 | Gertner | A61N 5/1017 378/65 |
| 2010/0039616 A1* | 2/2010 | Yumikake et al. | 351/206 |
| 2010/0142767 A1* | 6/2010 | Fleming | 382/117 |
| 2010/0149489 A1* | 6/2010 | Kikawa et al. | 351/206 |
| 2010/0189334 A1* | 7/2010 | Tomidokoro et al. | 382/131 |
| 2010/0194757 A1* | 8/2010 | Tomidokoro et al. | 345/440 |
| 2011/0080560 A1* | 4/2011 | Imamura et al. | 351/206 |
| 2011/0134392 A1* | 6/2011 | Iwase et al. | 351/206 |
| 2011/0267584 A1* | 11/2011 | Imamura et al. | 351/206 |
| 2012/0063660 A1* | 3/2012 | Imamura et al. | 382/131 |
| 2012/0070049 A1* | 3/2012 | Iwase et al. | 382/128 |
| 2012/0070059 A1* | 3/2012 | Furukawa et al. | 382/131 |
| 2012/0249956 A1* | 10/2012 | Narasimha-Iyer | A61B 3/102 351/206 |
| 2013/0057827 A1* | 3/2013 | Imamura et al. | 351/206 |
| 2013/0194545 A1* | 8/2013 | Ono | 351/206 |
| 2013/0195337 A1* | 8/2013 | Sakagawa | 382/131 |
| 2013/0258285 A1* | 10/2013 | Iwase et al. | 351/206 |
| 2014/0192324 A1* | 7/2014 | Straub et al. | 351/206 |

FOREIGN PATENT DOCUMENTS

| | | | |
|---|---|---|---|
| EP | 2189109 A | 5/2010 | |
| EP | 2189110 A1 * | 5/2010 | A61B 3/12 |
| JP | 2007-325831 A | 12/2007 | |
| JP | 2007325831 A * | 12/2007 | |
| JP | 2008-267892 A | 11/2008 | |
| JP | 2008-289579 A | 12/2008 | |
| JP | 2008-295804 A | 12/2008 | |
| JP | 2009-066015 A | 4/2009 | |

OTHER PUBLICATIONS

A. Fuller et al., "Segmentation of Three-dimensional Retinal Image Data", IEEE Transactions on Visualization and Computer Graphics, vol. 13, No. 6, Nov./Dec. 2007, p. 1719-1726.*

A. Bagci et al., "A Method for Detection of Retinal Layers by Optical Coherence Tomography Image Segmentation", 2007 IEEE/ NIH Life Science Systems and Applications Workshop (LISSA 2007), p. 144-147.*

Walter et al., "A Contribution of Image Processing to the Diagnosis of Diabetic Retinopathy—Detection of Exudates in Color Fundus Images of the Human Retina", IEEE Transactions on Medical Imaging. vol. 21. No. 10. Oct. 2002, pp. 1236-1243.

European Search Report issued in corresponding application No. 10783261.0 on Aug. 13, 2014.

Chinese Office Action issued in corresponding application No. 201080024522.5 on Sep. 26, 2013.

* cited by examiner

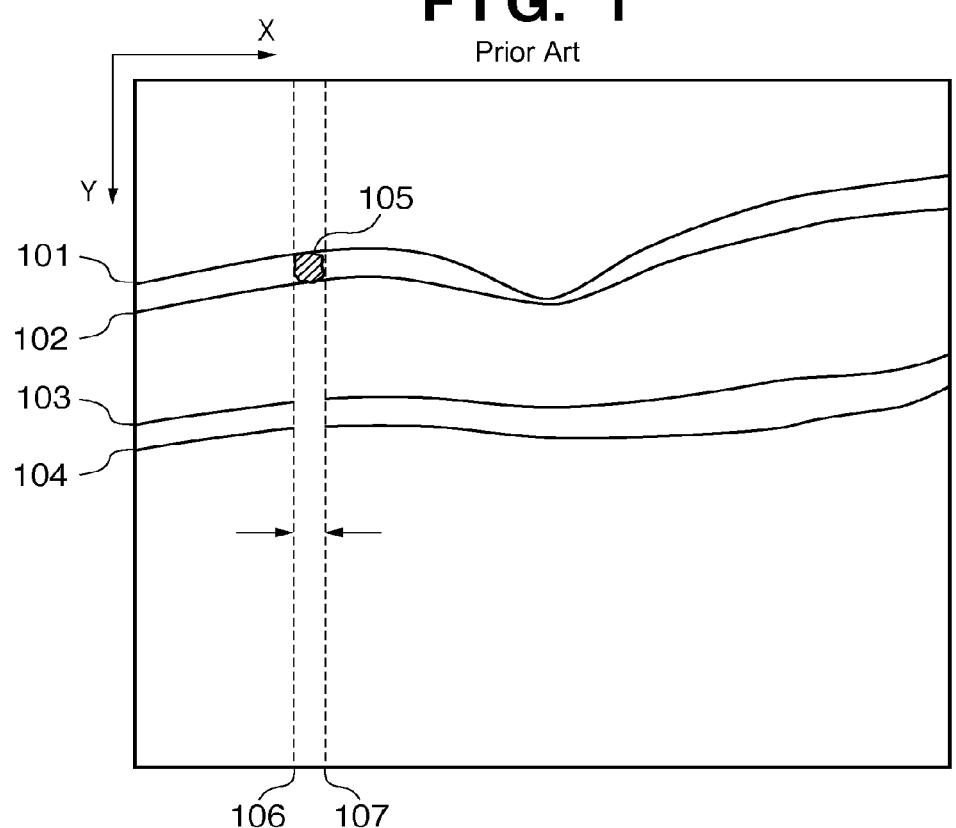
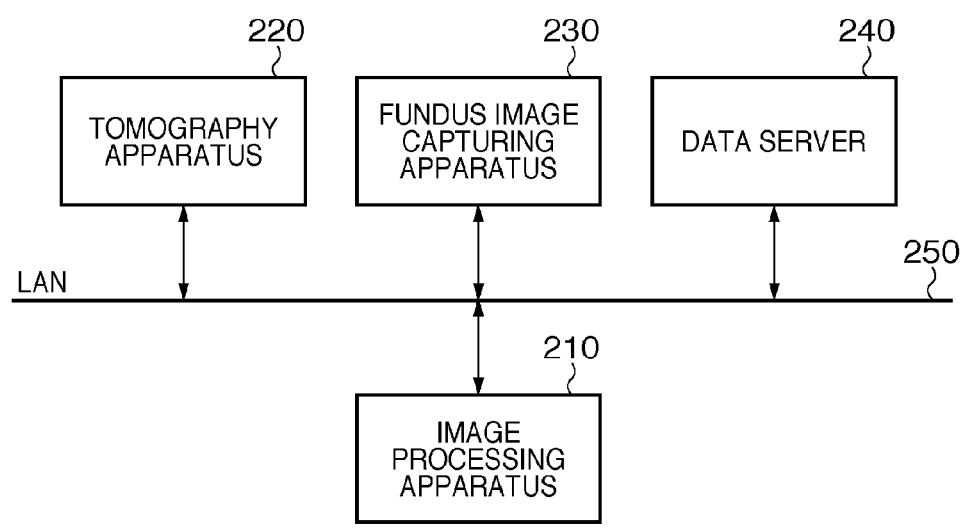

IMAGE PROCESSING APPARATUS FOR PROCESSING A TOMOGRAM OF AN EYE TO BE EXAMINED, IMAGE PROCESSING METHOD, AND COMPUTER-READABLE STORAGE MEDIUM

TECHNICAL FIELD

The present invention relates to an image processing apparatus, image processing method, and computer program, which assist an image diagnosis of an eye portion.

BACKGROUND ART

Ophthalmic examinations are commonly made for the early diagnosis of various diseases that come before lifestyle-related diseases and causes of blindness. A tomography apparatus for an eye portion such as an OCT (Optical Coherence Tomography) is expected to be effective to give more adequate diagnoses of diseases since it allows to three-dimensionally observe the state of the interior of retina layers.

A CAD (Computer-Aided-Diagnosis) technique using a computer is needed for the purpose of reducing the loads on diagnoses by doctors using the OCT. Functions required for the CAD for the OCT include, for example, a function of acquiring the three-dimensional (3D) position, shape, and distribution state of a morbid portion from an OCT image so as to grasp the degree of progress of a disease. Another example of the functions includes a function of presenting a temporal change associated with, for example, the shape of a morbid portion in correspondence with a set of OCT images of a single eye to be examined, which are captured at different times.

An image processing unit which implements such advanced diagnosis assistant functions is generally premised on that a morbid portion is extracted from an OCT image in pre-processing. Since the precision of analysis results to be presented is influenced according to this extraction precision of the morbid portion, implementation of high-precision morbid portion extraction processing has a very important implication. The present invention focuses attention on an exudate as one of lesions of eye portions.

A method to detect an exudate from a 3D OCT image with high precision has not been proposed yet. In general, an exudate has, as image features, a higher intensity than a surrounding portion and a massive structure. However, the OCT image includes locally high-intensity regions such as a nerve fiber layer, a junction between inner and outer photoreceptor segments, and a surrounding portion of a retinal pigment epithelium boundary in addition to the morbid portion. The current image quality of the OCT image does not have a sufficient contrast between the morbid portion and its surrounding portion. For this reason, it is difficult to extract an exudate with high precision by only focusing attention on the aforementioned image features.

As one solution for such problem, a region that is to undergo image analysis is limited in advance using information of the morbid portion obtained by another modality. A means for specifying a region to be limited in this way is disclosed in Japanese Patent Laid-Open No. 2007-325831.

FIG. 1 is a schematic view for explaining the invention disclosed in Japanese Patent Laid-Open No. 2007-325831, and shows a typical cross-sectional image (B-scan image) of an OCT image. FIG. 1 illustrates an inner limiting membrane 101, a boundary 102 between an optic nerve fiber layer (stratum opticum) and its underlying layer, a junction 103 between inner and outer photoreceptor segments, a retinal pigment epithelium boundary 104, and a blood vessel 105 in retina layers. In Japanese Patent Laid-Open No. 2007-325831, a blood vessel region is extracted from a fundus image of a single eye to be examined, so as to detect a blood vessel of an OCT image (not a morbid portion), and that position is projected onto the OCT image, thereby specifying a region where the blood vessel exists in the OCT image. As can be seen from FIG. 1, a region between broken lines 106 and 107 is a region obtained by projecting, onto the OCT image, the blood vessel region obtained from the fundus image, and the region where the blood vessel exists is specified.

SUMMARY OF INVENTION

With the invention described in Japanese Patent Laid-Open No. 2007-325831, an exudate existence range cannot be specified in the vertical direction of the OCT image (B-scan image) shown in FIG. 1. In addition, the OCT image suffers a problem of an insufficient contrast between a morbid portion and its surrounding portion based on the current image quality of the OCT image including high-intensity regions different from the morbid portion. Hence, the present invention provides a technique for extracting a morbid portion from an OCT image with high precision.

One aspect of embodiments of the present invention relates to an image processing apparatus comprising, boundary extraction means for detecting boundaries of retina layers from a tomogram of an eye to be examined, exudate extraction means for extracting an exudate region from a fundus image of the eye to be examined, registration means for performing registration between the tomogram and the fundus image, and calculating a spatial correspondence between the tomogram and the fundus image, specifying means for specifying a region where an exudate exists in the tomogram using the boundaries of the retina layers extracted by the boundary extraction means, the exudate region extracted by the exudate extraction means, and the spatial correspondence calculated by the registration means, likelihood calculation means for calculating likelihoods of existence of the exudate in association with the region specified by the specifying means, and tomogram exudate extraction means for extracting an exudate region in the tomogram from the region specified by the specifying means using the likelihoods.

Another aspect of embodiments of the present invention relates to an image processing apparatus comprising, boundary extraction means for detecting boundaries of retina layers from a tomogram of an eye to be examined, specifying means for specifying a region where an exudate exists in the tomogram using the boundaries of the retina layers extracted by the boundary extraction means, likelihood calculation means for calculating likelihoods of existence of the exudate in association with the region specified by the specifying means, and tomogram exudate extraction means for extracting an exudate region in the tomogram from the region specified by the specifying means using the likelihoods.

Further features of the present invention will become apparent from the following description of exemplary embodiments (with reference to the attached drawings).

BRIEF DESCRIPTION OF DRAWINGS

FIG. 1 is a view showing a typical tomogram of an OCT image;

FIG. 2 is a block diagram showing an example of the apparatus arrangement of an image processing system according to the first embodiment;

DESCRIPTION OF EMBODIMENTS

The best mode for carrying out the present invention will be described in detail hereinafter with reference to the drawings. However, the scope of the invention is not limited to illustrated examples.

First Embodiment

Figure 3:
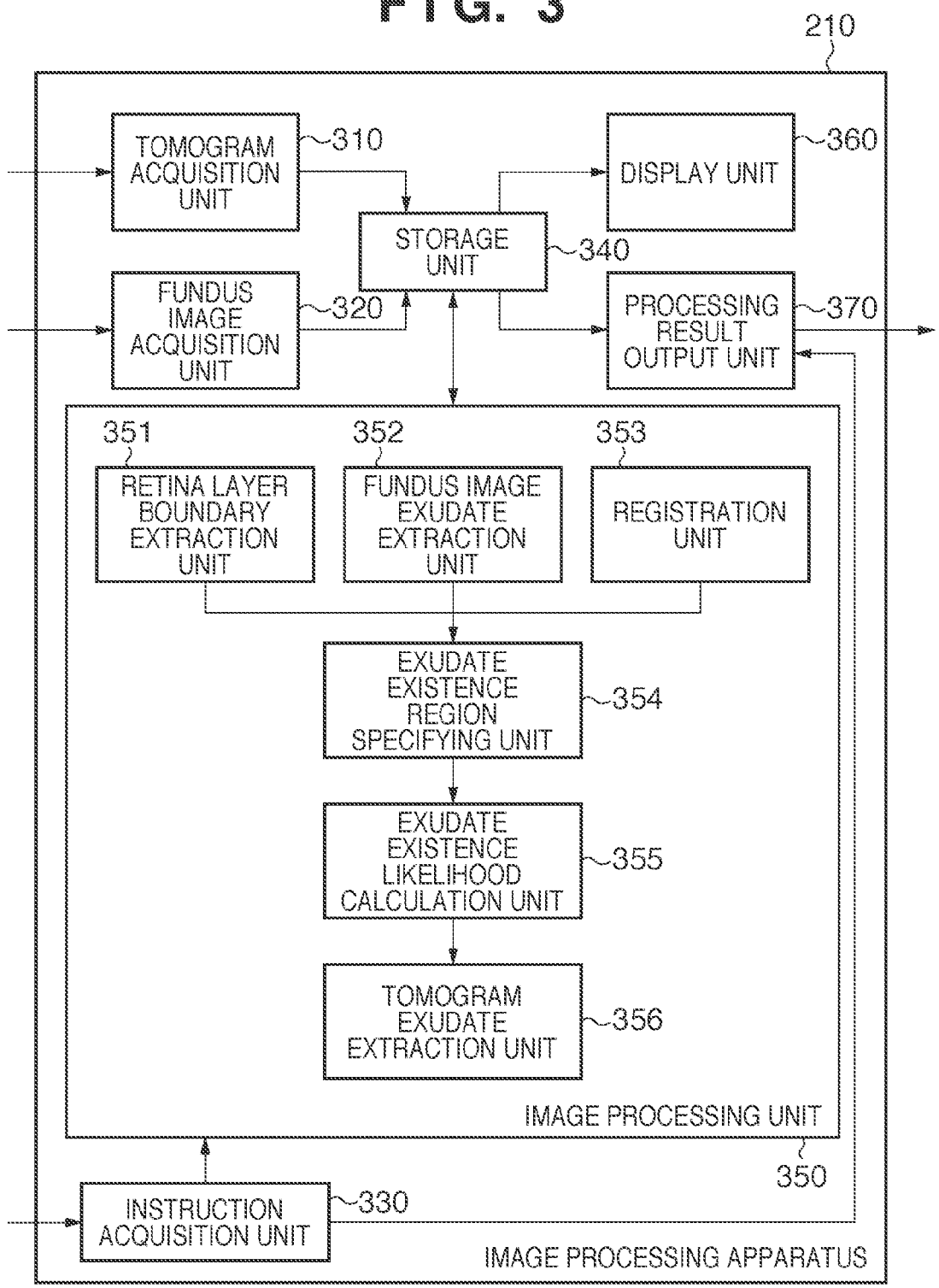
FIG. 3 is a block diagram showing an example of the functional arrangement of an image processing apparatus 210 according to the first embodiment.

The apparatus arrangement of an image processing system according to the first embodiment will be described below with reference to FIG. 2. An image processing apparatus 210 applies image processing to images captured by a tomography apparatus 220 and fundus image capturing apparatus 230, and images stored in a data server 240. The detailed arrangement of the image processing apparatus 210 is as shown in FIG. 3. The tomography apparatus 220 obtains a tomogram of an eye portion, and includes, for example, a time domain OCT or Fourier domain OCT. The tomography apparatus 220 three-dimensionally obtains a tomogram of an eye portion of an object (patient: not shown) according to operations of an operator (engineer or doctor: not shown). The acquired tomogram is transmitted to the image processing apparatus 210 and data server 240.

The fundus image capturing apparatus 230 captures a two-dimensional (2D) image of an eye fundus portion. The fundus image capturing apparatus 230 two-dimensionally captures an image of an eye fundus portion of an object (patient: not shown) according to operations of an operator (engineer or doctor: not shown). The acquired fundus image is transmitted to the image processing apparatus 210 and data server 240. The data server 240 stores tomograms acquired by the tomography apparatus 220 and fundus images captured by the fundus image capturing apparatus 230. Each stored image is transmitted to the image processing apparatus 210 in response to a request from the image processing apparatus 210 or an instruction from an operator (technician or doctor: not shown). Also, the data server 240 stores the processing results output from the image processing apparatus 210. A local area network (LAN) 250 interconnects the aforementioned apparatus. Note that these apparatus may be connected via an interface such as USB, IEEE1394, or an optical fiber.

The processing in the image processing apparatus 210 will be described below with reference to the block diagram shown in FIG. 3 and the flowchart shown in FIG. 4. This processing is implemented when respective blocks, which configure the image processing apparatus 210, execute corresponding processing programs.

In step S401, a tomogram acquisition unit 310 acquires a tomogram transmitted from the tomography apparatus 220 or that transmitted from the data server 240. The unit 310 transmits the acquired tomogram to a storage unit 340. In step S402, a fundus image acquisition unit 320 acquires a fundus image transmitted from the fundus image capturing apparatus 230 or that transmitted from the data server 240. The unit 320 transmits the acquired image to the storage unit 340.

In step S403, a retina layer boundary extraction unit 351 extracts boundaries of retina layers from the tomogram held in the storage unit 340. Since retina layers have different intensities in layers for respective layers, a contrast (edge) of density values is generated at a boundary between two neighboring layers. Hence, a layer boundary is extracted by focusing attention on this contrast. Various methods of extracting a region including such contrast are available. For example, a contrast is considered as an edge, and layer boundary extraction can be implemented by detecting the edge. More specifically, edge components are detected by applying an edge detection filter to a tomogram, and edges are searched from the vitreum side in the depth direction of an eye fundus. Then, a first peak position is detected as a boundary between the vitreum and retina layers, and a last peak position is detected as a retinal pigment epithelium boundary. A layer boundary may be detected using an active contour method such as Snakes or a level set method. In case of the level set method, a level set function higher by one dimension than dimensions of a region to be detected is defined, and a layer boundary to be detected is considered as a zero level line. A contour is controlled by updating the level set function, thus detecting a layer boundary. In addition, a layer boundary may be detected using a graph theorem such as GraphCut.

In case of the layer detection processing using the graph theorem, nodes corresponding to respective pixels of an image and terminals called a sink and source are set, and edges which couple between nodes (n-link) and those which couple between terminals (t-link) are set. A layer boundary is detected by calculating a minimum cut based on a graph that is created by giving weights to these edges. Any of the above layer boundary extraction methods may be three-dimensionally applied to the entire 3D tomogram as an object to be processed, or may be independently applied to each 2D tomogram while considering an input 3D tomogram as a set of 2D tomograms. Note that the method of detecting a layer boundary is not limited to these methods, and any other methods may be used as long as they can detect a layer boundary from a tomogram of an eye portion.

In step S404, a fundus image exudate extraction unit 352 extracts an exudate from the fundus image held in the storage unit 340. As image features, an exudate region locally exists in the fundus image, and has higher intensities than a surrounding region. Thus, an exudate is extracted by focusing attention on such image features. Various extraction methods may be used. For example, a method of applying tophat operations to one of R, G, and B components of the fundus image is available. The tophat operations calculate density value differences for respective pixels between an original image and output image obtained by applying morphological operations to a density image. In the image after application of the tophat operations, since pixels included in an exudate have signals higher than other pixels, an exudate region can be extracted by applying threshold processing to this image.

As another exudate region extraction method, an identifier such as a Support Vector Machine (SVM) and an identifier ensemble built by, for example, AdaBoost may be used. In this case, whether or not each pixel belongs to an exudate is determined based on, as feature amounts, the output results of various image filters which can emphasize a region in which density values of R, G, and B components of the fundus image or intensity contrasts in R, G, and B components are high using the identifier or its ensemble. Furthermore, all pixels, which are determined to belong to the exudate, undergo clustering to identify whether or not each cluster belongs to an exudate region. At this time, an average or variance of intensities in each cluster or a intensity contrast between regions inside and outside each cluster is used as a feature amount. With the aforementioned processing, the exudate region can be extracted. When a region extracted by the exudate extraction processing does not sufficiently include an exudate, figure dilation processing for the extraction result or a region expansion method using the extracted region as a seed (seed point) is applied to acquire a region that sufficiently includes an exudate. Note that the method of extracting an exudate from a fundus image is not limited to these methods, and any other methods may be used as long as they can extract an exudate from a fundus image.

Figure 8:
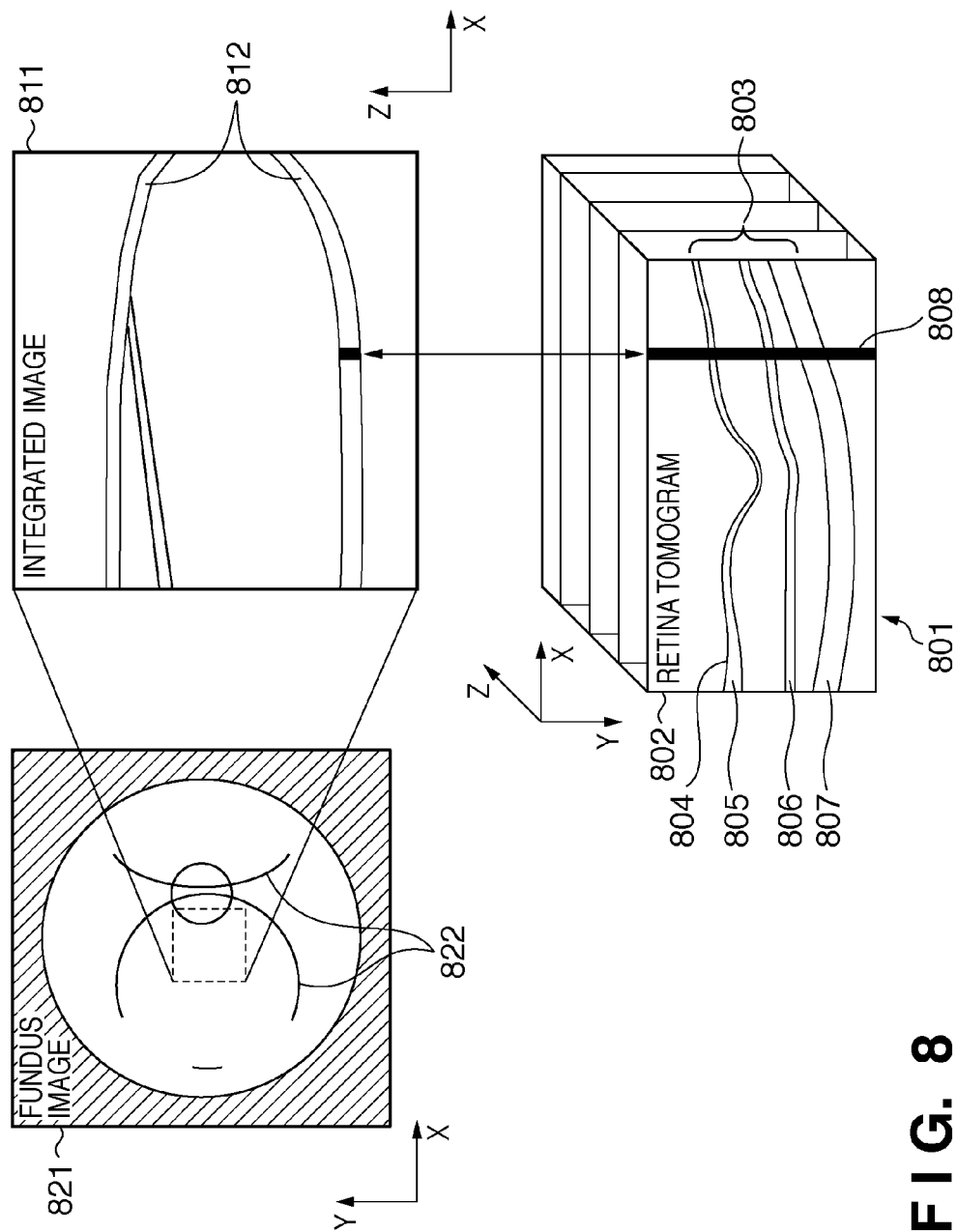
FIG. 8 is a view for explaining the relationship among a fundus photo, retina volume data, and integrated image.

In step S405, a registration unit 353 performs registration between the tomogram and fundus image held in the storage unit 340. An integrated image is generated from the tomogram. Generation of the integrated image will be described below with reference to FIG. 8. Referring to FIG. 8, retina volume data 801 includes a plurality of retina tomograms 802. As a coordinate system of the retina volume data 801, a lateral direction of each retina tomogram 802 (pattern diagram) is defined as an x-axis, a longitudinal direction is defined as a y-axis, and the arrangement direction of the retina tomograms 802 is defined as a z-axis. Especially, a direction along the y-axis is called an A-scan line, an x-y plane is called a B-scan section, and an x-z plane is called a C-scan section. As a coordinate system of a fundus image 821, a lateral direction is defined as an X-axis, and a longitudinal direction is defined as a Y-axis. Reference numeral 804 denotes an inner limiting membrane; 805, a lower side of a nerve fiber layer; 806, an upper side of an outer plexiform layer; and 807, a lower side of a retinal pigment epithelium. Retina layers 803 are defined as layers, which exist in an anatomy sandwiched between the inner limiting membrane 804, and the lower boundary of the retinal pigment epithelium.

An integrated image 811 is generated by integrating intensities of voxels of the retina volume data 801 in the Z-axis direction. More specifically, a projection plane parallel to the C-scan section of the tomogram is assumed, and density values are projected onto corresponding pixels on the projection plane for respective A-scan lines of the retina tomograms 802. A calculation method of a pixel value to be projected may use a method of calculating a maximum value or minimum value of voxel values on each A-scan line, a method of simply adding voxel values in the A-scan line direction, or a method of calculating an average by dividing the sum of voxel values by the number of additions. Also, not all voxels on each A-scan line need be considered, and pixel values to be projected may be calculated within an arbitrary range.

Next, regions having anatomic features are extracted from the integrated image 811 and fundus image 821. As one of typical anatomic features, this embodiment focuses attention on a blood vessel. Since a blood vessel has a thin linear structure, a blood vessel is extracted using a filter which emphasizes the linear structure. As the filter which emphasizes the linear structure, a differential filter such as a Sobel filter or Laplacian filter may be used. Alternatively, a line segment emphasizing filter based on a contrast, which calculates a difference between an average value of image density values in a line segment assumed as a structural element, and an average value in a local region that surrounds the structural element, may be used. Alternatively, eigenvalues of a Hessian matrix are calculated for respective pixels of a density value image, and a linear region may be extracted based on combinations of two eigenvalues that are obtained as results. Furthermore, tophat operations that simply have a line segment as a structural element may be performed. In FIG. 8, blood vessel regions 812 of the eye fundus are extracted from the integrated image 811, and blood vessel regions 822 are extracted from the fundus image 821.

Finally, the coordinate system (X, Y) of the fundus image 821 and the coordinate system (x, z) of the integrated image 811 are registered using the blood vessel regions 812 and 822 respectively extracted from the integrated image 811 and fundus image 821, thereby calculating a spatial correspondence between the tomograms 802 and fundus image 821. Note that a blood vessel projection region 808 is a pixel region having coordinates (x, z) on the retina tomogram 802. Upon performing the registration, an evaluation value that represents a similarity between two images is defined in advance, and images are deformed to obtain the best evaluation value. As the evaluation value, a value which represents a degree of overlapping between the integrated image blood vessel regions 812 and the fundus image blood vessel regions 822 obtained by the above processing, a distance between corresponding landmarks upon focusing attention on regions having characteristic geometric shapes such as branch portions of blood vessels, and the like can be used. In this embodiment, a blood vessel is used as a region having an anatomic feature. Alternatively, another anatomic feature such as an optic papilla region, or an exudate or bleeding region caused by a disease may be used. Furthermore, in place of focusing attention on only anatomic features such as blood vessels, an evaluation value calculated from the entire images, for example, a mean square error, correlation coefficient, or mutual information content of intensities may be used. Note that when the tomograms and fundus images have already been registered by a state-of-the-art technique, this step S405 may be omitted.

In step S406, an exudate existence region specifying unit 354 specifies a region where an exudate is likely to exist in the tomogram. The region is specified using the extraction results of the boundaries of the retina layers obtained by the retina layer boundary extraction unit 351, the extraction result of the exudate on the fundus image obtained by the fundus image exudate extraction unit 352, and the spatial correspondence between the tomograms and fundus image obtained by the registration unit 353.

Figure 5:
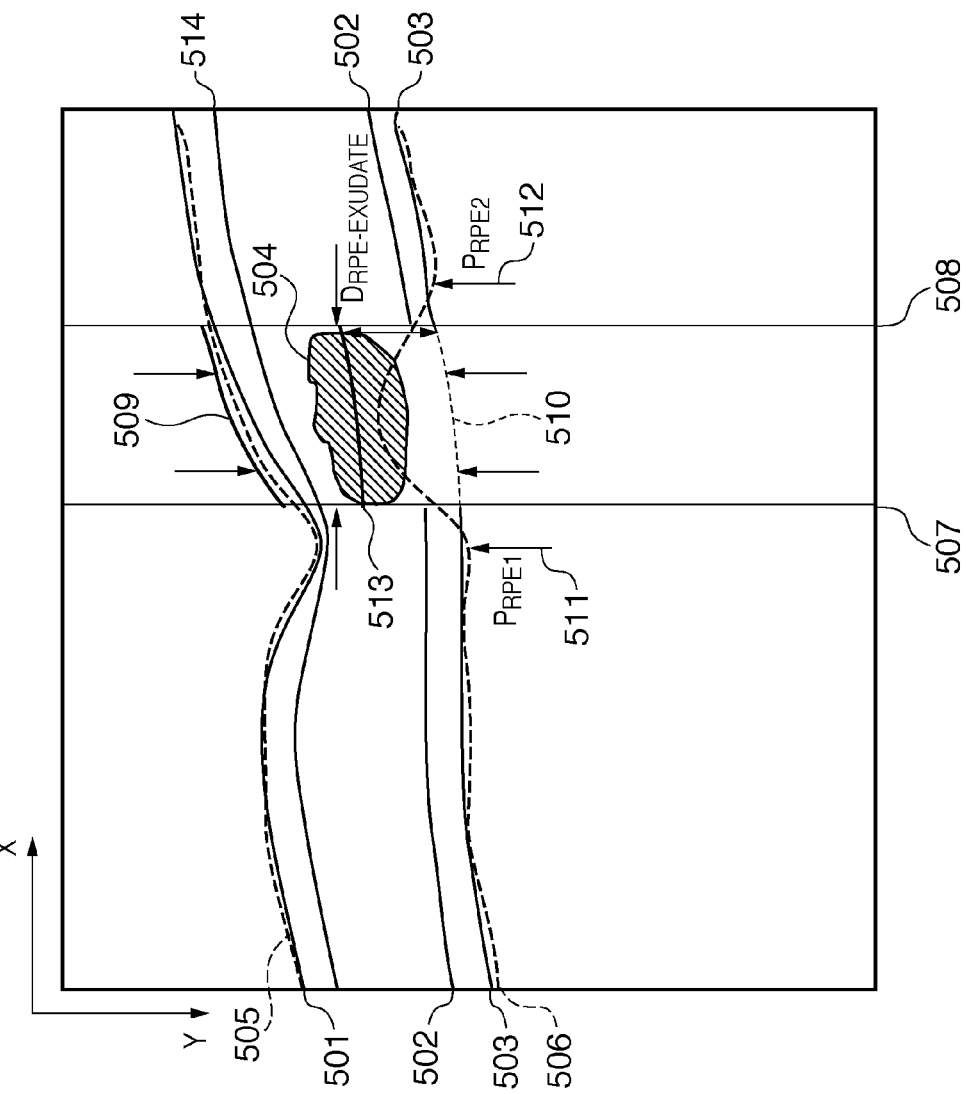
FIG. 5 is a view for explaining the operation of an exudate existence region specifying unit 354 according to the first embodiment.

The operation of the exudate existence region specifying unit 354 will be described below with reference to FIG. 5. FIG. 5 shows an image obtained by superimposing one typical slice of a B-scan image of the tomograms held in the storage unit 340, and the extraction results of the boundaries of the retina layers obtained by the retina layer boundary extraction unit 351. Referring to FIG. 5, reference numeral 501 denotes an inner limiting membrane; 514, a boundary between an optic nerve fiber layer and its underlying layer; 502, a junction between inner and outer photoreceptor segments; and 503, a retinal pigment epithelium boundary. Also, reference numeral 504 denotes an exudate. Furthermore, reference numeral 505 denotes an extraction result of the inner limiting membrane obtained by the retina layer boundary extraction unit 351; and 506, an extraction result of the retinal pigment epithelium boundary obtained by the retina layer boundary extraction unit 351.

An exudate existence likelihood in the present invention is a value defined for each pixel in the tomogram, and represents a likelihood indicating if that pixel belongs to an exudate. More specifically, a higher likelihood indicates that the pixel belongs to an exudate, and a lower likelihood indicates that it does not belong to an exudate. The existence likelihood is defined in only a local region that is expected to sufficiently include an exudate. In step S406, this local region is set. The local region is set using the boundaries of the retina layers extracted from the tomogram of the eye portion and the exudate region extracted from the fundus image. Settings of four boundary line segments 507, 508, 509, and 510 required to define the local region will be described below.

The two line segments 507 and 508 required to define the local region in a direction perpendicular to the A-scan line (the X-axis direction in FIG. 5) define boundaries of a corresponding region of an exudate region obtained by projecting the exudate region extracted from the fundus image onto the tomogram. The upper boundary line segment 509 in a direction parallel to the A-scan line (the Y-axis direction in FIG. 5) defines a line segment in a region sectioned by the aforementioned boundary line segments 507 and 508 of the inner limiting membrane 505 extracted from the tomogram. In FIG. 5, the boundary line segment 509 is expressed by a bold solid line, which indicates a portion sectioned by the boundary line segments 507 and 508 of the inner limiting membrane extraction result indicated by a broken line. Finally, upon decision of the lower boundary line segment 510 in the direction parallel to the A-scan line (the Y-axis direction in FIG. 5), the extraction result of the retinal pigment epithelium boundary cannot be simply used. This is because the junction between inner and outer photoreceptor segments and the retinal pigment epithelium which are located below the exudate in the tomogram of the eye portion tend to have lower intensities than their surrounding region, as also shown in FIG. 5. In such case, when the exudate region is erroneously extracted as the retinal pigment epithelium boundary, and this result is simply used, a region which sufficiently includes the exudate cannot be set.

In order to solve this problem, according to the present invention, the boundary line segment 510 is defined using extraction results $p_{RPE1}$ and $p_{RPE2}$ 510 of the retinal pigment epithelium boundary in the vicinity of a region bounded by the boundary line segments 507 and 508. More specifically, a line segment is generated by interpolating between $p_{RPE1}$ and $p_{RPE2}$ using a known interpolation method, and is used as the boundary line segment 510. In this embodiment, the extraction result 505 of the inner limiting membrane and the extraction result 506 of the retinal pigment epithelium boundary are used to decide the boundary line segments 509 and 510. However, the extraction results of the boundaries of the retina layers that can be used in this embodiment are not limited to those. For example, an extraction result of the boundary 514 between the optic nerve fiber layer and its underlying layer and that of the junction 502 between inner and outer photoreceptor segments may be used.

In step S407, an exudate existence likelihood calculation unit 355 calculates exudate existence likelihoods for respective pixels in the local region which is bounded by the boundary line segments 507, 508, 509, and 510 acquired by the exudate existence region specifying unit 354. As is generally known, an exudate exists between the outer plexiform layer and the junction between inner and outer photoreceptor segments. According to the present invention, existence likelihoods are assigned based on this anatomic knowledge. Various setting methods of existence likelihoods are available. In this embodiment, positions where an exudate is most likely to exist are estimated from the line segment 510 acquired by interpolation, and likelihoods are assigned based on that result. More specifically, positions 513 separated upward from respective pixels on the boundary segment line 510 by a predetermined distance $D_{RPE\text{-}EXUDATE}$ along the A-scan line are defined as positions where an exudate anatomically exists. The value $D_{RPE\text{-}EXUDATE}$ may be determined from a representative distance value from an exudate to the retinal pigment epithelium boundary in typical cases including an exudate. Also, the value $D_{RPE\text{-}EXUDATE}$ may be calculated based on an average of distance values from intermediate positions between the outer plexiform layer and the junction between inner and outer photoreceptor segments to the retinal pigment epithelium boundary.

A position $p_{EXUDATE}$ estimated that an exudate is most likely to exist is used as a reference position, and a likelihood is set to assume 1 within a predetermined range from that reference position and 0 outside the range, as given by:

$$C(p) = \begin{cases} 0 & (|p - p_{EXUDATE}| \le h_{EXUDATE}) \\ 1 & (|p - p_{EXUDATE}| > h_{EXUDATE}) \end{cases} \quad (1)$$

where p represents the coordinates of a certain voxel on the A-scan line, and $p_{EXUDATE}$ represents the coordinates of the position 513 estimated that an exudate is most likely to exist on the A-scan line. Also, $h_{EXUDATE}$ is an average value of the sizes (distance values from the barycenters of exudates) of exudates, and is acquired from exudate regions included in a plurality of tomograms acquired in advance. In equation (1), the likelihood is defined by a binary value (0 or 1). However, the likelihood may be given by a multi-value equal to or larger than 0 to equal to or smaller than 1. A likelihood is defined by a Gaussian function, as given by:

$$C(p) = \exp(-(p - p_{EXUDATE}))^2 \quad (2)$$

Alternatively, a likelihood may assume a value simply inversely proportional to a distance value from the reference position 513 or may be set to be a value inversely proportional to a square of the distance value, as given by:

$$C(p) = \frac{1}{|p - p_{EXUDATE}| + 1} \quad (3)$$

$$C(p) = \frac{1}{(p - p_{EXUDATE})^2 + 1} \quad (4)$$

Furthermore, an image feature amount such as a filter output value of a point convergence index filter may be used as an existence likelihood, or a likelihood may be set based on a combination with the line segment 509.

In step S408, a tomogram exudate extraction unit 356 extracts an exudate based on the exudate existence likelihoods acquired by the exudate existence likelihood calculation unit 355. Voxels which belong to the exudate have relatively high intensities in the tomogram, and the entire exudate has a massive structure in the tomogram. The exudate is extracted using these image features and the existence likelihoods. Let I(p) be a tomogram intensity of a voxel p, and C(p) be an existence likelihood. Also, let F(p) be a filter output value of a point convergence index filter as one of filters which emphasize a region having a massive structure.

$$F(p) = \max_{R_1 \leq r \leq R_2} \sum_{v \in V[r,D]} v \cdot g(p+v) \quad (5)$$

where v is one element of a set $V^{[r, D]}$ of directional vectors which indicate respective voxels in a ring defined by two concentric circles having radii r and r+D, and g(p+v) is a intensity gradient vector of the tomogram at a voxel p+v. Also, '·' represents an inner product of two vectors. $R_1$ and $R_2$ are radii of an inner concentric circle of two concentric circles, and exudates having different sizes can be extracted by applying the point convergence index filter while changing the radius of the concentric circle. Note that as a filter which emphasizes a region having a massive structure, an output result of the tophat operations may be used, and a intensity contrast obtained based on differences between intensities of a circle having a voxel p of interest as a center and its surrounding region may be used. Furthermore, these filters may be a 2D filter which can be independently applied to each B-scan image of the tomogram, or they may be a 3D filter which can be applied to the entire tomogram. Then, an exudate region $R_{EXUDATE}$ is extracted by applying threshold processing to at least one value of C(p), I(p), and F(p). This embodiment will explain an example using all of C(p), I(p), and F(p).

$$R_{EXUDATE} = \{p \in V_{OCT} | C(p) = T_C, I(p) \geq T_I, F(p) \geq T_F\} \quad (6)$$

where $V_{OCT}$ represents a set including voxels in the tomogram as elements. $T_C$, $T_I$, and $T_R$ can be decided from preliminary experiments using a plurality of tomograms which have already been acquired in advance. More specifically, an extraction failure ratio $E_{FN}$ and an extraction error ratio $E_{FP}$ of an exudate when a set of values as $T_C$, $T_I$, and $T_R$ are given. Using the calculation result, an evaluation value E is calculated, as defined by:

$$E = E_{FN} + E_{FP} \quad (7)$$

The evaluation values E are calculated while changing $T_C$, $T_I$, and $T_R$. $T_C$, $T_I$, and $T_R$ which can minimize E are used as thresholds of equation (6). The exudate extraction method is not limited to the threshold processing for C(p), I(p), and F(p). More specifically, an identifier may be built using an SVM or AdaBoost to have C(p), I(p), and F(p) as feature amounts, and exudate extraction may be implemented using the obtained identifier. In this case, a plurality of feature amounts are further added. For example, an average value, variance, degree of distortion, kurtosis, entropy, Sobel filter, Laplacian filter, Gaussian filter, maximum value filter, and minimum value filter for the tomogram and existence likelihood image may be added. Also, an output value of a filter as a combination of these feature amounts can be used as a feature amount.

In step S409, a display unit 360 displays, on a monitor, the tomogram acquired by the tomogram acquisition unit 310, the fundus image acquired by the fundus image acquisition unit 320, and the exudate region obtained by an image processing unit 350. In step S410, a processing result output unit 370 transmits information required to identify the eye to be examined, the tomogram and fundus image input to the image processing unit 350, and the exudate region obtained by the image processing unit 350 to the data server 240.

According to the aforementioned arrangement, the image processing system specifies a region where an exudate is more likely to exist using the extraction results of the boundaries of the retina layers acquired from the OCT tomogram and the exudate extraction result acquired from the fundus image. Then, the system decides existence likelihoods in that region. Finally, the system extracts an exudate based on the existence likelihoods and image features obtained from the OCT tomogram. As a result, the exudate region can be extracted with high precision.

Second Embodiment

This embodiment will explain an example of a modification in which exudate existence likelihoods in step S407 of the first embodiment are set based on previous knowledge about correlation information between the distances between the boundaries of retina layers and existence likelihoods. The apparatus arrangement of an image processing system corresponding to this embodiment is the same as that shown in FIGS. 2 and 3. In the first embodiment, a highest existence likelihood is assigned to a position separated from a retinal pigment epithelium boundary by a given distance $R_{PE-EXUDATE}$, and smaller existence likelihoods are assigned with increasing distance from this position. However, an inner limiting membrane—retinal pigment epithelium boundary distance varies depending on objects. Even in a single object, the distance varies depending on locations in an eye fundus. For this reason, the aforementioned existence likelihood setting method is unlikely to appropriately assign likelihoods to positions where an exudate exists. Hence, in this embodiment, the relationships between the inner limiting membrane—retinal pigment epithelium boundary distances and existence likelihoods are acquired in advance from a plurality of eyes to be examined, and these pieces of information are stored in a data server 240. That is, the data server 240 stores a plurality of sets of likelihoods of respective pixels between the inner limiting membranes and retinal pigment epithelium boundaries in association with the inner limiting membrane—retinal pigment epithelium boundary distances. Upon calculating existence likelihoods for a new eye to be examined, which are not stored in the data server 240, an exudate existence likelihood calculation unit 355 uses the relationships between the inner limiting membrane—retinal pigment epithelium boundary distances and existence likelihoods, which are stored in the data server 240.

Previous knowledge about correlation information between the inner limiting membrane—retinal pigment epithelium boundary distances and existence likelihoods is acquired from a large number of tomograms that are stored in advance. Initially, an exudate existence region in each tomogram is manually extracted. Inner limiting membrane—retinal pigment epithelium boundary distances are measured in association with respective A-scan lines which pass through the extracted region. With the above processing, the inner limiting membrane—retinal pigment epithelium boundary distances and a one-dimensional label image (an image including a value "1" of a voxel which belongs to an exudate and a value "0" as other voxel values) which expresses voxels that belong to the exudate on the A-scan lines can be acquired.

After the inner limiting membrane—retinal pigment epithelium boundary distances and exudate label images are acquired by applying the aforementioned processing to all tomograms, correlations between the inner limiting membrane—retinal pigment epithelium boundary distances and exudate existence positions are calculated. More specifically, a mean $M^{[d]}(p)$ of label values is calculated for each voxel in association with label images $L^{[d]}_i(p)$ on the A-scan lines having a distance value d as the inner limiting membrane—retinal pigment epithelium boundary distance, as given by:

$$M^{[d]}(p) = \frac{\sum_{i \in S_d} L_i^{[d]}(p)}{N^{[d]}} \quad (8)$$

where $S_d$ is a set of indices indicating label images on the A-scan lines having the distance value d as the inner limiting membrane—retinal pigment epithelium boundary distance, and i represents a certain index. Also, $N^{[d]}$ is the number of A-scan lines having the distance value d. The mean $M^{[d]}(p)$ of the label values obtained by equation (8) is defined as an exudate existence likelihood on the A-scan lines having the distance value d.

Figure 6:
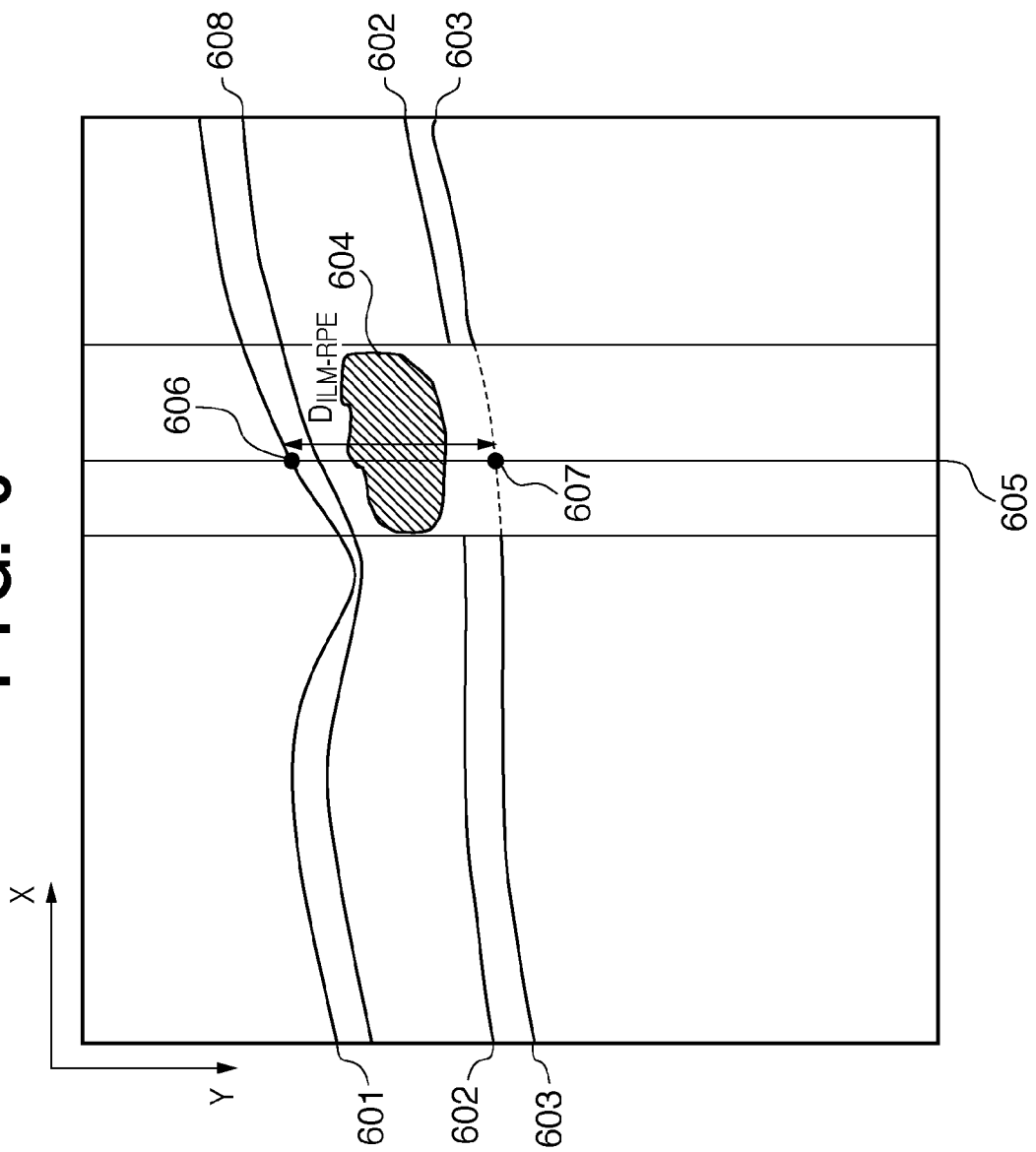
FIG. 6 is a view for explaining calculations of exudate existence likelihoods according to the second embodiment.

Step S407 of calculating exudate existence likelihoods will be described below with reference to FIG. 6. A distance $D_{ILM-RPE}$ between boundary line segments 509 and 510 acquired in step S406 is calculated for each A-scan line which passes through a local region. FIG. 6 practically illustrates a certain A-scan line 605, and a distance between an intersection 606 between this A-scan line 605 and an inner limiting membrane and an intersection 607 between the A-scan line 605 and a retinal pigment epithelium boundary is $D_{ILM-RPE}$. Next, exudate existence likelihoods $M^{[DILM-RPE]}(p)$ at respective voxels on the A-scan line when the distance between the inner limiting membrane and retinal pigment epithelium boundary is $D_{ILM-RPE}$ are acquired from a database. The acquired exudate existence likelihoods are substituted in corresponding voxels p. By executing these operations for all A-scan lines which pass through the local region, the exudate existence likelihoods can be set in all voxels in the local region.

In this embodiment, exudate existence likelihoods are set based on correlation information associated with the inner limiting membrane—retinal pigment epithelium boundary distances and exudate existence positions. However, another anatomic information may be used. For example, a distance value r from a macula in the tomogram may be used. In this case, an exudate existence likelihood is a value $M^{[r]}(p)$ decided based on the distance value r from a macula. Furthermore, two parameters d and r may be combined, and an existence likelihood in this case is a value $M^{[d,r]}(p)$ decided based on d and r. In this embodiment, the inner limiting membrane—retinal pigment epithelium boundary distance is used as a distance between the boundaries of retina layers. However, the distance between the boundaries of retina layers that can be used in this embodiment is not limited to such specific distance. For example, a distance between a boundary 608 between an optic nerve fiber layer and its underlying layer and a junction 602 between inner and outer photoreceptor segments may be used.

According to the aforementioned arrangement, high-precision exudate extraction can be implemented without being influenced by differences of inner limiting membrane—retinal pigment epithelium boundary distances between objects and differences of distances in the eye fundus in a single object.

Third Embodiment

Figure 4:
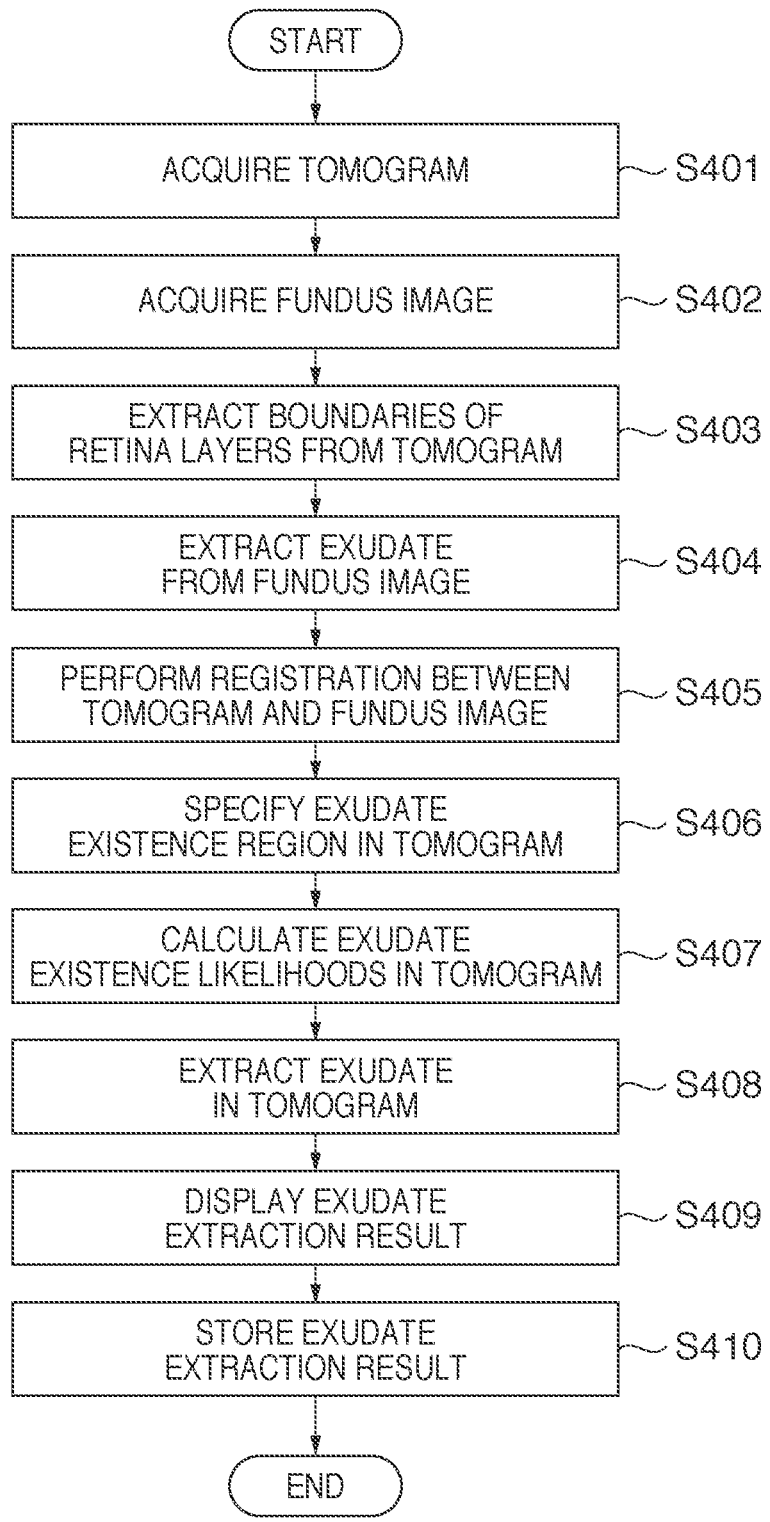
FIG. 4 is a flowchart showing an example of the processing of the image processing apparatus 210 according to the first embodiment.

This embodiment will explain an example in which extraction error determination about a region extracted by exudate extraction in a tomogram in step S408 in FIG. 4 is made. In step S406, a region to which exudate extraction processing is to be applied is limited using an exudate region acquired from a fundus image in addition to retina layer extraction results. For this reason, when a region other than an exudate in the fundus image is erroneously extracted as an exudate, the exudate extraction processing is unwantedly applied to a region where no exudate exists in the tomogram. This embodiment will be described in detail below.

Figure 9:
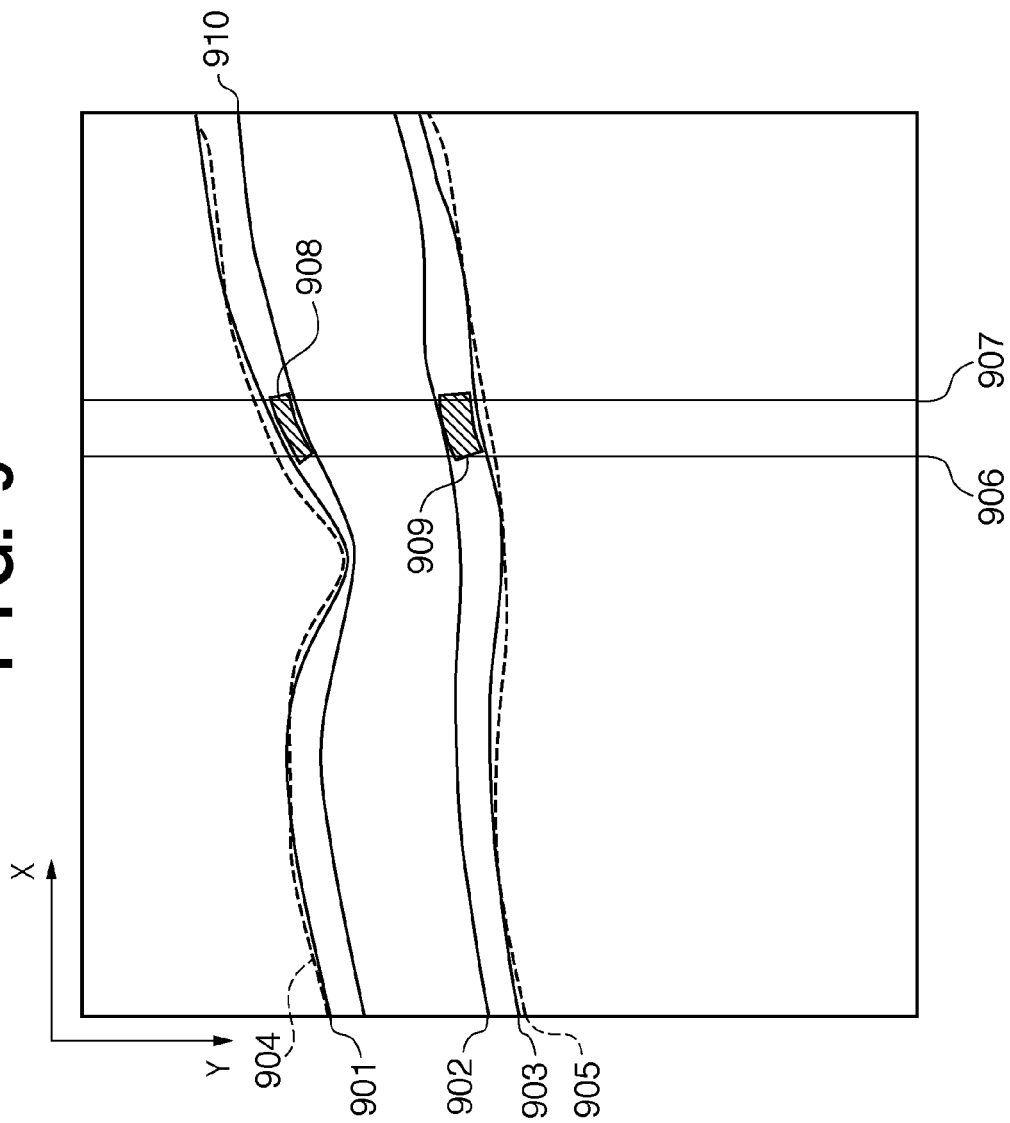
FIG. 9 is a view for explaining a determination error of exudate extraction according to the third embodiment.

FIG. 9 is a view for explaining the aforementioned extraction error. Referring to FIG. 9, reference numeral 901 denotes an inner limiting membrane; 910, a boundary between an optic nerve fiber layer and its underlying layer; 902, a junction between inner and outer photoreceptor segments; and 903, retinal pigment epithelium boundary. Also, reference numeral 904 denotes an extraction result of the inner limiting membrane obtained by a retina layer boundary extraction unit 351; and 905, an extraction result of the retinal pigment epithelium boundary obtained by the retina layer boundary extraction unit 351. When a region where no exudate exists is erroneously extracted from a fundus image, a normal region where no exudate exists is set as a region where an exudate is likely to exist in step S406, and exudate existence likelihoods are set in this region in step S407 like in a region bounded by lines 906 and 907 in FIG. 9. As a result, upon extracting an exudate in step S408, a portion 908 of the optic nerve fiber layer (a region bounded by lines 901 and 910 in FIG. 9) or a portion 909 of a region bounded by the junction between inner and outer photoreceptor segments and the boundary of the retina layer is likely to be erroneously extracted as an exudate. Since a region having a spherical massive structure is extracted as an exudate in step S408, a region having such layer structure is unlikely to be erroneously extracted, but it is difficult to suppress all extraction errors.

Thus, it is determined whether or not a region extracted in step S408 is an erroneously extracted region. If it is determined that the extracted region is an erroneously extracted region, that region is deleted, and is not included in an exudate region. More specifically, the number of coupled pixels is calculated for each extracted coupled region, and is compared with a coupling threshold. If the number of coupled pixels is smaller than the coupling threshold, that region is determined as a small region, and is deleted. On the other hand, as for regions each having the number of coupled pixels equal to or larger than the coupling threshold, a degree of circularity is calculated for each region, and a region having the degree of circularity lower than a predetermined degree is determined as an erroneously extracted region and is deleted. In place of using the degree of circularity, eigenvalues of a Hessian matrix for a B-scan image may be calculated, whether or not a coupled region has a circular density value distribution may be determined based on a combination of eigenvalues, and an erroneously extracted region may be deleted using the determination result. Note that this embodiment can be applied to an exudate extraction error about a region which has image features similar to an exudate in a fundus image but has different image features in a tomogram like a druse.

According to the aforementioned arrangement, this embodiment can suppress extraction errors in exudate extraction, and can implement exudate extraction with high precision.

Fourth Embodiment

The image processing apparatus 210 according to the aforementioned embodiments specifies a region where an exudate is more likely to exist using the boundaries of retina layers extracted from a tomogram and an exudate region extracted from a fundus image. Within this region, exudate existence likelihoods are calculated, and an exudate is finally extracted from the tomogram based on the exudate existence likelihoods and image features. An image processing apparatus according to this embodiment limits an exudate extraction processing target region, calculates existence likelihoods based on anatomic knowledge, and extracts an exudate based on the existence likelihoods and image features, as in the first embodiment. However, in the first embodiment, upon limiting the exudate extraction processing target region, a projection region obtained by projecting an exudate region extracted from a fundus image onto a tomogram is used in addition to tomogram retina layer extraction results. By contrast, this embodiment limits a target region using only the tomogram retina layer extraction results without using any 2D image such as a fundus image.

Figure 11:
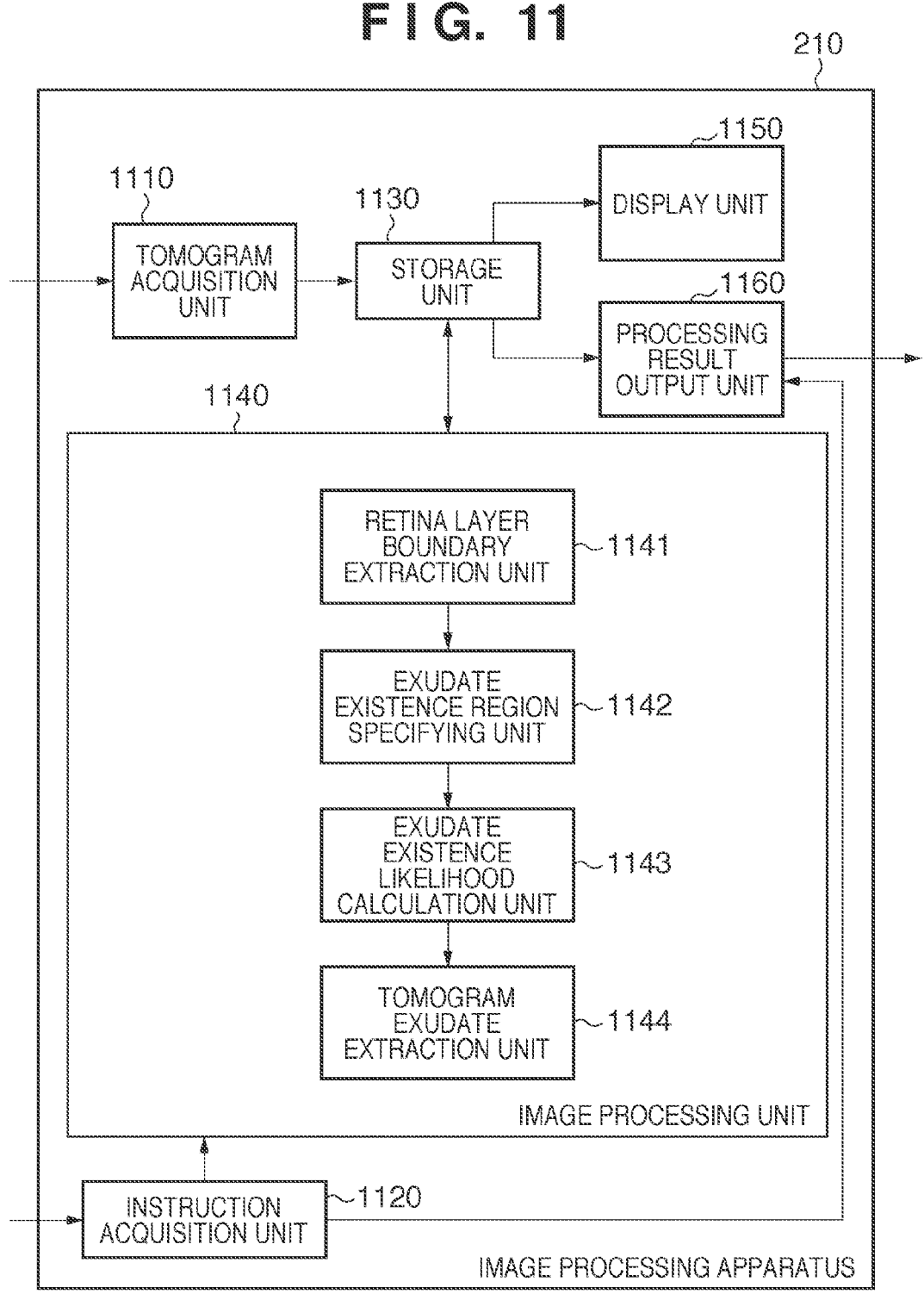
FIG. 11 is a block diagram showing an example of the functional arrangement of an image processing apparatus 210 according to the fourth embodiment.

The functional arrangement of an image processing apparatus 210 according to this embodiment will be described below with reference to FIG. 11. FIG. 11 is a functional block diagram of the image processing apparatus 210. The image processing apparatus 210 includes a tomogram acquisition unit 1110, instruction acquisition unit 1120, storage unit 1130, image processing unit 1140, display unit 1150, and processing result output unit 1160. Furthermore, the image processing unit 1140 includes a retina layer boundary extraction unit 1141, exudate existence region specifying unit 1142, exudate existence likelihood calculation unit 1143, and tomogram exudate extraction unit 1144. Since all the units except for the exudate existence region specifying unit 1142 are the same as those in the functional arrangement of the image processing apparatus 210 according to the first embodiment, a description thereof will not be repeated. The exudate existence region specifying unit 1142 specifies a region where an exudate is likely to exist in the tomogram from retina layer extraction results output from the retina layer boundary extraction unit 1141.

The processing sequence of the image processing apparatus 210 of this embodiment will be described below. The processing in this embodiment can be implemented by executing steps S401, S403, S406, S407, and S408 to S410 of steps of the flowchart shown in FIG. 4. Of these steps, steps S401, S403, and S408 to S410 have the same processing contents. The processes in steps S406 and S407 corresponding to this embodiment will be described below.

Figure 10:
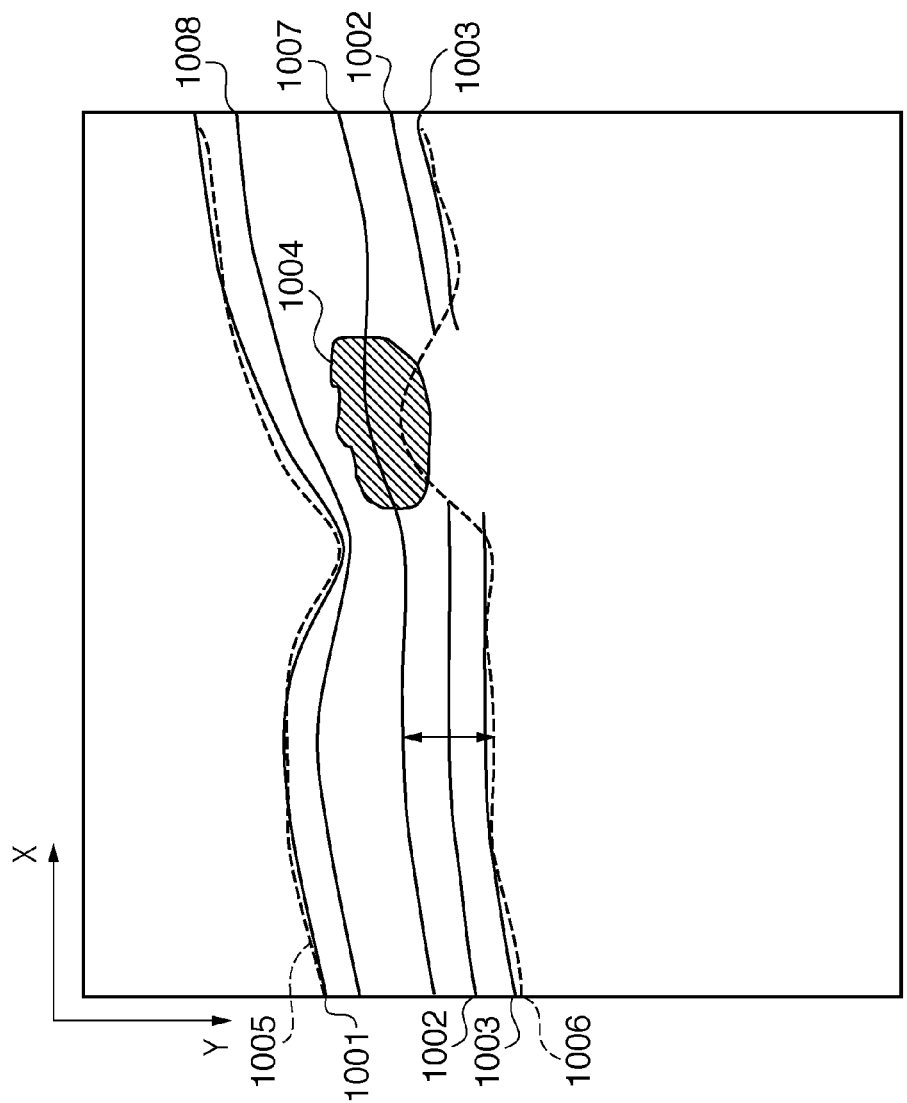
FIG. 10 is a view for explaining calculations of exudate existence likelihoods according to the fourth embodiment.

In step S406, the exudate existence region specifying unit 1142 specifies a region where an exudate is likely to exist from information of boundaries of retina layers acquired by the retina layer boundary extraction unit 1141. An exudate existence region specifying method in this case will be described below with reference to FIG. 10. Referring to FIG. 10, reference numeral 1001 denotes an inner limiting membrane; 1008, a boundary between an optic nerve fiber layer and its underlying layer; 1002, a junction between inner and outer photoreceptor segments; and 1003, a retinal pigment epithelium boundary. Reference numeral 1004 denotes an exudate. Furthermore, reference numeral 1005 denotes an extraction result of the inner limiting membrane obtained by the retina layer boundary extraction unit 1141; and 1006, an extraction result of the retinal pigment epithelium boundary obtained by the retina layer boundary extraction unit 1141.

In this embodiment, exudate existence likelihoods are defined in a region having, as boundaries, the extraction result 1005 of the inner limiting membrane and the extraction result 1006 of the retinal pigment epithelium boundary, which are obtained by the retina layer boundary extraction unit 1141. Based on anatomic knowledge "an exudate exists between an outer plexiform layer and the junction between inner and outer photoreceptor segments", existence likelihoods are assigned to voxels in this region. Initially, positions 1007 where an exudate is most likely to exist are decided for respective A-scan lines in a B-scan image based on the extraction result 1005 of the inner limiting membrane and the extraction result 1006 of the retinal pigment epithelium boundary. FIG. 10 illustrates, as the positions 1007, a line segment which connects positions where an exudate is most likely to exist. Note that a slightly broader region on the upper side of the extraction result 1005 of the inner limiting membrane and on the lower side of the extraction result 1006 of the retinal pigment epithelium boundary may be set in consideration of a possibility that the extraction result 1005 of the inner limiting membrane and the extraction result 1006 of the retinal pigment epithelium boundary do not sufficiently include an exudate. In this embodiment, the extraction result 1005 of the inner limiting membrane and the extraction result 1006 of the retinal pigment epithelium boundary are used as the extraction results of the boundaries of the retina layers required to specify an exudate existence region. However, the extraction results of the boundaries of the retina layers that can be used in this embodiment are not limited to these specific extraction results. For example, the extraction result of the boundary 1008 between the optic nerve fiber layer and its underlying layer and that of the junction 1002 between inner and outer photoreceptor segments may be used.

In step S407, the exudate existence likelihood calculation unit 1143 calculates exudate existence likelihoods for respective pixels around the positions 1007 where an exudate is most likely to exist, which is acquired by the exudate existence region specifying unit 1142. As is generally known, an exudate exists between the outer plexiform layer and the junction between inner and outer photoreceptor segments. According to the present invention, existence likelihoods are assigned based on this anatomic knowledge. This embodiment can calculate exudate existence likelihoods as in the first embodiment using the positions 1007 as the positions 513 in FIG. 5 of the first embodiment.

According to the aforementioned arrangement, the image processing system specifies a region where an exudate is more likely to exist using only the extraction results of the boundaries of the retina layers, which are acquired from an OCT tomogram initially. Then, the system decides existence likelihoods in that region based on the extraction results of the boundaries of the retina layers. Finally, the system extracts an exudate based on the existence likelihoods and image features obtained from the OCT tomogram. As a result, an exudate region can be extracted with high precision.

Other Embodiments

The aforementioned embodiments implement the present invention as an image processing apparatus. However, an embodiment of the present invention is not limited to only the image processing apparatus. This embodiment implements the present invention as software which runs on a computer.

Figure 7:
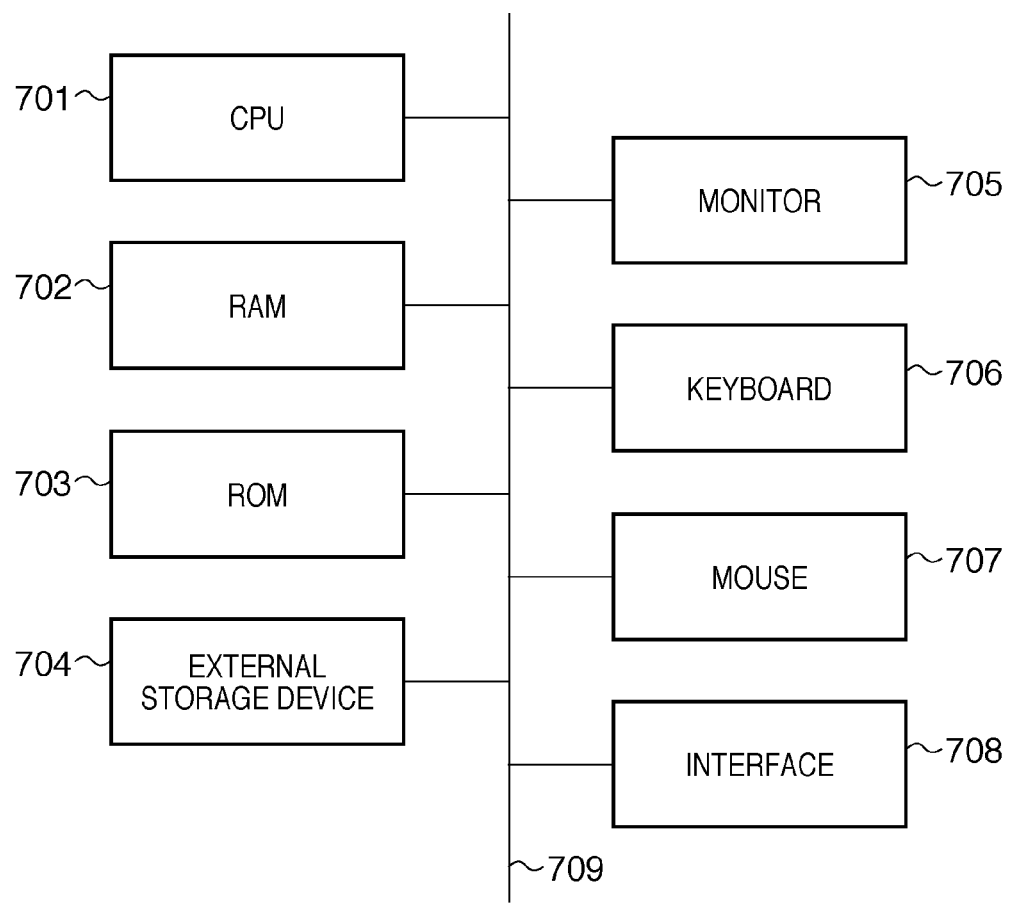
FIG. 7 is a block diagram showing the basic arrangement of a computer which implements functions of the image processing apparatus 210.

FIG. 7 is a block diagram showing the basic arrangement of a computer used to implement the functions of respective units of an image processing apparatus 210 as software. A CPU 701 controls the overall computer using programs and data stored in a RAM 702 and ROM 703. Also, the CPU 701 implements the functions of the respective units by controlling execution of software programs corresponding to the respective units of the image processing apparatus 210. The RAM 702 includes an area for temporarily storing programs and data loaded from an external storage device 704, and also an area required for the CPU 701 to execute various processes. The function of a storage unit 340 is implemented by the RAM 702 and the like. The ROM 703 generally stores a BIOS, setting data, and the like of the computer.

The external storage device 704 serves as a large-capacity information storage device such as a hard disk drive, and stores an operating system and computer programs executed by the CPU 701. The external storage device 704 stores information which is given in the description of this embodiment, and such information is loaded onto the RAM 702 as needed. A monitor 705 is configured by, for example, a liquid crystal display. For example, the monitor 705 can display the contents output from a display unit 360. A keyboard 706 and mouse 707 are input devices. An operator can input various instructions to the image processing apparatus 210 using these input devices. The function of an instruction acquisition unit 330 is implemented via these input devices. An interface 708 is used to exchange various data between the image processing apparatus 210 and external apparatus, and is configured by, for example, an optical fiber, IEEE1394, USB, or Ethernet® port. Data acquired via the interface 708 is fetched onto the RAM 702. Functions of a tomogram acquisition unit 310, fundus image acquisition unit 320, and processing result output unit 370 are implemented via the interface 708. The aforementioned components are interconnected via a bus 709.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-133453, filed Jun. 2, 2009 which is hereby incorporated by reference herein in its entirety.

The invention claimed is:

1. An image processing apparatus comprising:
at least one memory; and
at least one processor to perform operations comprising:
extracting boundaries of retina layers from a tomogram of an eye to be examined;
extracting an exudate region from a fundus image of the eye to be examined;
specifying a region where an exudate exists in the tomogram using the extracted boundaries of the retina layers and the extracted exudate region;
calculating, according to distances between the extracted boundaries of the retina layers, likelihoods of existence of the exudate in the specified region of the tomogram; and
extracting, according to voxels having intensities higher than a threshold and the calculated likelihoods, an exudate region in the specified region of the tomogram.

2. The apparatus according to claim 1, wherein the operations further comprise deciding a region in the tomogram corresponding to the exudate region extracted from the fundus image by projecting the extracted exudate region onto the tomogram, and
wherein the region where the exudate exists is specified in the tomogram based on the boundaries of the retina layers included in the corresponding region and a surrounding region thereof.

3. An image processing apparatus comprising:
at least one memory; and
at least one processor to perform operations comprising:
extracting boundaries of retina layers from a tomogram of an eye to be examined;
specifying a region where an exudate exists in the tomogram using a fundus image of the eye to be examined and the extracted boundaries of the retina layers;
calculating, according to distances between the extracted boundaries of the retina layers, likelihoods of existence of the exudate in the specified region of the tomogram; and
extracting, according to voxels having intensities higher than a threshold and the calculated likelihoods, an exudate region in the specified region of the tomogram.

4. The apparatus according to claim 1, wherein in the calculating, the likelihoods are calculated according to the distances from a reference position, wherein the reference position is decided based on the boundaries of the retina layers in the specified region.

5. The apparatus according to claim 1, wherein in the calculating, likelihoods of pixels in the specified region are decided by acquiring, from a data server which stores a set of likelihoods of respective pixels that exist between the boundaries of the retina layers in association with the distances between the boundaries of the retina layers, the set of likelihoods according to the distances between the boundaries of the retina layers in the specified region.

6. The apparatus according to claim 1, wherein in the extracting an exudate region in the specified region of the tomogram, respective pixels which are included in the specified region and have the likelihoods larger than a related threshold are extracted as the exudate region in the tomogram.

7. The apparatus according to claim 1, wherein in the extracting an exudate region in the specified region of the tomogram, at least one of intensities of pixels and output values of a filter configured to emphasize a region in which intensities are higher than a surrounding region are used, in addition to the likelihoods, and pixels larger than related thresholds in association with the likelihoods and at least one of the intensities and the output values of the filter are extracted as the exudate region in the tomogram.

8. The apparatus according to claim 1, wherein when a number of coupled pixels is smaller than a coupling threshold or a degree of circularity is lower than a predetermined degree in a coupled region obtained by coupling pixels extracted as an exudate, the coupled region as the exudate region in the tomogram is not extracted.

9. An image processing method comprising:
extracting boundaries of retina layers from a tomogram of an eye to be examined;
extracting an exudate region from a fundus image of the eye to be examined;
specifying a region where an exudate exists in the tomogram using the extracted boundaries of the retina layers, and the extracted exudate region;
calculating, according to distances between the extracted boundaries of the retina layers, likelihoods of existence of the exudate in the specified region of the tomogram; and
extracting, according to voxels having intensities higher than a threshold and the calculated likelihoods, an exudate region in the specified region of the tomogram.

10. An image processing method comprising:
extracting boundaries of retina layers from a tomogram of an eye to be examined;
specifying a region where an exudate exists in the tomogram using a fundus image of the eye to be examined and the extracted boundaries of the retina layers;
calculating, according to distances between the extracted boundaries of the retina layers, likelihoods of existence of the exudate in the specified region of the tomogram; and
extracting, according to voxels having intensities higher than a threshold and the calculated likelihoods, an exudate region in the specified region of the tomogram.

11. A non-transitory computer-readable storage medium storing a computer program for making a computer perform operations comprising:
extracting boundaries of retina layers from a tomogram of an eye to be examined;
extracting an exudate region from a fundus image of the eye to be examined;
specifying a region where an exudate exists in the tomogram using the extracted boundaries of the retina layers and the extracted exudate region;
calculating, according to distances between the extracted boundaries of the retina layers, likelihoods of existence of the exudate in the specified region of the tomogram; and
extracting, according to voxels having intensities higher than a threshold and the calculated likelihoods, an exudate region in the specified region of the tomogram.

12. A non-transitory computer readable storage medium storing a computer program for making a computer perform operations comprising:
extracting boundaries of retina layers from a tomogram of an eye to be examined;
specifying a region where an exudate exists in the tomogram using a fundus image of the eye to be examined and the extracted boundaries of the retina layers;
calculating, according to distances between the extracted boundaries of the retina layers, likelihoods of existence of the exudate in the specified region of the tomogram; and
extracting, according to voxels having intensities higher than a threshold and the calculated likelihoods, an exudate region in the specified region of the tomogram.

13. The apparatus according to claim 1, wherein the operations further comprise performing registration between the tomogram and the fundus image, and
wherein the region where an exudate exists is specified in the tomogram after the registration.

14. The apparatus according to claim 3, wherein the operations further comprise performing registration between the tomogram and the fundus image, and
wherein the region where an exudate exists is specified in the tomogram after the registration.

15. The image processing method according to claim 9, further comprising performing registration between the tomogram and the fundus image,
wherein the region where an exudate exists in the tomogram is specified by the specifying after the performance of the registration.

16. The image processing method according to claim 10, further comprising performing registration between the tomogram and the fundus image,
wherein the region where an exudate exists in the tomogram is specified by the specifying after the performance of the registration.

17. The apparatus according to claim 1, wherein each likelihood of each voxel is calculated according to the distances.

18. The apparatus according to claim 3, wherein each likelihood of each voxel is calculated according to the distances.

19. The image processing method according to claim 9, wherein each likelihood of each voxel is calculated according to the distances.

20. The image processing method according to claim 10, wherein each likelihood of each voxel is calculated according to the distances.

* * * * *